(12) United States Patent
Venter (10) Patent No.: US 8,781,771 B1
(45) Date of Patent: Jul. 15, 2014

(54) MEASUREMENT OF MATERIAL PROPERTIES

(76) Inventor: Liebrecht Rudolph Venter, Haymarket, VA (US)

( * ) Notice: Subject to any disclaimer, the term of this patent is extended or adjusted under 35 U.S.C. 154(b) by 227 days.

(21) Appl. No.: 12/931,426

(22) Filed: Feb. 1, 2011

Related U.S. Application Data (60) Provisional application No. 61/337,181, filed on Feb. 1, 2010.

(51) Int. Cl.
*G01R 25/00* (2006.01)
*G01R 27/26* (2006.01)

(52) U.S. Cl.
USPC ............................................. 702/65; 324/663

(58) Field of Classification Search
USPC .................. 702/65, 57, 66–67, 72, 127, 137, 702/188–189; 324/76.77, 452, 519, 324/521–522, 525, 600, 622, 650, 654, 658, 324/663–664, 683, 686, 691, 693–694, 709
See application file for complete search history.

(56) References Cited

U.S. PATENT DOCUMENTS

| | | | | |
|---|---|---|---|---|
| 6,703,847 | B2 * | 3/2004 | Venter et al. | 324/663 |
| 6,989,678 | B2 * | 1/2006 | Venter et al. | 324/663 |
| 2008/0161972 | A1 * | 7/2008 | Magill | 700/275 |

* cited by examiner

*Primary Examiner* — Toan Le (57) ABSTRACT

A system and method employing a general impedance as a cost-effective detector to measure dielectric properties of a material at both high and low frequencies, using combinations of resistance, capacitance, and inductance. The method may be applied in a wood drying installation including a kiln as coaxial cable element for a data transmission, wherein metal walls and doors of the kiln grounded to the soil include the outer coaxial conductor (shield) relative to a substantially isolated axial central conductor. The method is further suitable for determining the fiber saturation point of wood by measuring the loss tangent of the wood and determining the point where the time derivative of the loss-tangent equals zero, which corresponds to the fiber saturation point of the wood.

19 Claims, 9 Drawing Sheets

FIGURE 1. The equivalent circuit of Wood

FIGURE 2. The general lumped model

| $f$ (Hz) | Density in oven-dry condition $\rho_0$ (g/cm³) | $t$ (°C) | Moisture content (%) | | | | | | | | | | | |
|---|---|---|---|---|---|---|---|---|---|---|---|---|---|---|
| | | | 0 | | 10 | | 20 | | 30 | | 60 | | 100 | |
| | | | $\varepsilon'_\perp$ | $tg\delta_\perp$ | $\varepsilon'_\perp$ | $tg\delta_\perp$ | $\varepsilon'_\perp$ | $tg\delta_\perp$ | $\varepsilon'_\perp$ | $tg\delta_\perp$ | $\varepsilon'_\perp$ | $tg\delta_\perp$ | $\varepsilon'_\perp$ | $tg\delta_\perp$ |
| $10^4$ | 0.3 | −20 | 1.6 | 0.013 | 2.4 | 0.04 | 4.9 | 0.3 | 6.0 | 0.6 | 8.5 | 0.75 | 10.6 | 1.05 |
| | | +20 | 1.7 | 0.008 | 2.9 | 0.09 | 7.7 | 3.3 | 13.7 | 6 | 39 | 6 | 56 | 6 |
| | | 50 | 1.8 | 0.007 | 3.2 | 0.31 | 9.8 | 8.3 | 19.5 | 13.2 | 59 | 11.4 | 90 | 9.6 |
| | | 90 | 2.0 | 0.005 | 3.7 | 0.59 | 12.6 | 14.9 | − | 22.8 | 85 | 18.6 | 134 | 14.4 |
| | 0.4 | −20 | 1.8 | 0.016 | 3.0 | 0.06 | 6.3 | 0.4 | 7.9 | 0.8 | 11 | 1.0 | 13.8 | 1.4 |
| | | +20 | 1.9 | 0.010 | 3.6 | 0.12 | 9.9 | 4.4 | 18 | 8 | 52 | 8 | 74 | 8 |
| | | 50 | 2.0 | 0.008 | 4.0 | 0.41 | 12.6 | 11.0 | 26 | 17.6 | 79 | 15.2 | 118 | 12.8 |
| | | 90 | 2.2 | 0.006 | 4.6 | 0.79 | 16.1 | 19.8 | − | 30.4 | 114 | 24.8 | 178 | 19.2 |
| | 0.5 | −20 | 2.0 | 0.019 | 3.5 | 0.07 | 7.7 | 0.5 | 9.7 | 1.0 | 13.5 | 1.3 | 17 | 1.8 |
| | | +20 | 2.1 | 0.012 | 4.2 | 0.15 | 12.1 | 5.5 | 22 | 10 | 65 | 10 | 92 | 10 |
| | | 50 | 2.3 | 0.010 | 4.7 | 0.51 | 15.4 | 13.8 | 31 | 22 | 98 | 19 | 147 | 16 |
| | | 90 | 2.5 | 0.007 | 5.4 | 0.99 | 19.7 | 24.8 | − | 38 | 142 | 31 | 221 | 24 |
| | 0.6 | −20 | 2.3 | 0.022 | 4.0 | 0.08 | 9.2 | 0.6 | 11.4 | 1.2 | 16 | 1.5 | 20.2 | 2.1 |
| | | +20 | 2.4 | 0.014 | 4.8 | 0.18 | 14.4 | 6.6 | 26 | 12 | 77 | 12 | 109 | 12 |
| | | 50 | 2.6 | 0.011 | 5.4 | 0.61 | 18.3 | 16.5 | 37 | 26.4 | 116 | 22.8 | 174 | 19.2 |
| | | 90 | 2.8 | 0.008 | 6.1 | 1.19 | 23.5 | 29.7 | − | 45.6 | 168 | 37.2 | 262 | 29 |
| | 0.7 | −20 | 2.5 | 0.026 | 4.6 | 0.10 | 10.9 | 0.7 | 13.6 | 1.4 | 18.5 | 1.75 | 23.4 | 2.5 |
| | | +20 | 2.7 | 0.016 | 5.5 | 0.21 | 17 | 7.7 | 31 | 14 | 90 | 14 | 123 | 14 |
| | | 50 | 2.9 | 0.013 | 6.2 | 0.71 | 22 | 19.25 | 44 | 30.8 | 136 | 26.6 | 197 | 22.4 |
| | | 90 | 3.2 | 0.009 | 7.0 | 1.39 | 28 | 34.7 | − | 53.2 | 197 | 43.4 | 295 | 33.6 |

FIGURE 3. The dielectric constant $\epsilon$ and loss-tangent $\tan\delta$ of wood at frequency $40 kHZ$ at different moisture contents and temperatures FIGURE 4. The dielectric constant $\epsilon$ manifested as a capacitance $C_x$ correlated to moisture content $M.C$, Conductivity $\sigma$ and Loss-tangent $\tan\delta$ of 4 wood stacks during a typical drying run FIGURE 5. Configuration of Kiln as Co-Axial element for data and power transmission FIGURE 6. Configuration of Kiln as Co-Axial element supplying data and power to measurement instrumentation

MEASUREMENT OF MATERIAL PROPERTIES

CROSS-REFERENCE TO RELATED APPLICATIONS

This application claims benefit of U.S. Provisional Application No. 61/337,181, filed Feb. 1, 2010, the disclosure of which, including the specification, drawings, and claims is incorporated by reference in its entirety.

TECHNICAL FIELD

The present invention relates to a method of using a general impedance as a cost-efficient detector for measuring the moisture content and fiber saturation point of wood. To achieve this, a wood drying kiln is used as a co-axial cable to efficiently provide data and power to the measuring units containing the detectors.

BACKGROUND OF THE INVENTION

When drying wood in a wood drying kiln, an end-point moisture content of 5% to 20% is normally required. Traditional methods of measuring the moisture content of wood, whilst reasonably accurate towards the end-point moisture content, become less accurate at higher values of the moisture content. At a moisture content of above 30%, the traditional methods become completely unreliable.

For the proper control of the environment in which wood is dried, for example, in a wood-drying kiln, it is important for the moisture content of the wood to be known accurately while the moisture content is still relatively high, e.g. above 30%. If the moisture content is accurately known at these relatively high values it becomes possible to accelerate the drying process considerably, without causing undue stresses in the wood.

The complexity of wood is easily underestimated. Wood is highly an-isotropic both in anatomy and by its electrical and dielectric properties. It is a complex composition of air, water cell-wall structure, organic materials such as cellulose, lignin and resins, inorganic salts. The anatomy is comprised of solid cell-wall structures combined with trachea (tangential hollow tubes) which is either filled with water or air depending on the moisture content (m.c.) of the sample. Furthermore, variations within species are remarkably striking regarding ion-content which translates in conductivity and resistive variations. Species-to-species variations in ion content is even more influential and wide species to species changes in conductivity is experienced.

In order to measure the dielectrics of such a complex medium, the influences of each of these components need be addressed before valuable and usable measurements and methods can be devised. The measurement of the dielectric properties of wood is particularly and unexpectedly troublesome as reported in detail by Torgovnikov[T]. (The citations herein identified by upper case letters are the bibliography at the end of the specification.) Not only is the dielectric highly an-isotropic and grain direction dependent, the unexpected temperature behavior of the conductivity of wood is worth mentioning. It would be expected that wood would have similar characteristics as usual carbon based resistors, which displays a decrease in conductivity with increased temperature (increase in resistance respectively). The conductivity of wood in fact does not follow this trend at all, but rather displays the temperature dependence strikingly similar to a semi-conductor i.e. the conductance increases with increasing temperature. It is clear that if this is not taken into account, measuring methods of, e.g., capacitance of the wood-dielectric will fail at elevated temperatures as large errors will be introduced. This particular fact resulted in several measurement systems to fail in industry for obvious reasons James [R]. To make matters even more troublesome, extremely non-linear anomalies occur regarding the other relevant dielectric components, namely the relative permittivity $\in_r$ also known in layman's terms as the dielectric constant.

Since the relative permittivity gives rise to capacitance via the probe geometry and since capacitance will be what is measured, this influence will be discussed in terms of the capacitance but is equally valid for the relative permittivity. Dielectric constant and as a consequence capacitance increases substantially with increase in temperature compared to more homogeneous dielectrics. However, Torgovnikov [C] cites James's results to display the following anomalies. Not only is the relative permittivity and therefore capacitance wildly frequency dependent, it does so in an unexpected manner. Completely dry (bone-dry) wood has a relative permittivity of 4, while water has a relative permittivity of 80. The relative permittivity of water and bone-dry wood is for all purposes frequency independent except for the normal dispersion variations not of relevance here. However, when water and wood is combined i.e. wet wood is measured, we do not obtain the intuitive combined relative permittivity of 84, but instead values are reported by Torgovnikov and James [C] of $\in_r=650000$ at certain lower frequencies. This is most certainly an anomaly and to date still unexplained and seemingly not challenged however unlikely it seems. Furthermore the relative permittivity and therefore the capacitance increases dramatically with decrease in frequency compared to minimal change in $\in_r$ detected for pure water and bone-dry wood when not in combination over the same frequency range. In addition the loss-tangent tan $\delta$, which is an indication of how lossy a material is in an applied electromagnetic field, also displays curious anomalies generally not expected from dielectric media. Even the most complex composites usually has a loss-tangent, for which each value of loss-tangent only one value of element of composition can be obtained. With wood as dielectric the loss-tangent generally becomes a relation i.e. the loss-tangent plotted against moisture content is that of a bell-curve Torgovnikov [C] resulting in two moisture contents giving the same loss-tangent reading. This clearly cancels loss-tangent for measurement above f.s.p. in most cases as it results in ambiguity. These complications dwarfs the already significant an-isotropic behavior of $\in_r$ which has different values when the applied electromagnetic field is applied tangential and radially to the wood respectively. The remaining significant behavior of the wood-water relationship is at f.s.p, where free water starts to assemble in the hollow trachea and dissolves salts. These ions then drastically increase the conductivity above f.s.p. to enormous proportions and in effect making any correlation of moisture content above f.s.p. difficult if not impossible. The conductivity of wood therefore becomes an almost constant high value above f.s.p. literally independent of higher moisture contents. The reason for the sudden conductivity increase above f.s.p. is due to the minerals K, P, Al, Fe, Zn, Ca, Mn, Cl, Na and Mg, to name a few which are naturally encountered in wood. The majority of these minerals are dissolved and present in the free water as ions and therefore has a phenomenal influence on conductivity above f.s.p. Below f.s.p. no free water exists and these minerals are then deposited on the cell walls with less influence.

The bounded water (adsorbed water on cell walls) is also changed fundamentally in that the water which is now adsorbed by the cell-walls clearly cannot be rotated easily as a dipole in the applied field. As the wood dries the adsorption to the cell-walls increases giving even more resistance to rotation in the applied electromagnetic field. This results in a curved relationship between $\in_r$ at moisture contents below f.s.p. Above f.s.p. the free water in the hollow trachea are the dominant influence on $\in_r$ and $\in_r$ versus moisture content and the water molecules as dipole can easily and unrestrictedly be oriented in the applied electromagnetic field. This is the reason why $\in_r$ is then linear from f.s.p upwards to 200%. This combined then establishes a curve-linear relationship between $\in_r$ and the moisture content as empirically verified by Skaar[F]. It is therefore evident that two "types" of water exists in the wood-water combination and they influence the dielectric properties in a very different way. The list of behavioral anomalies are not exhausted as there are piezzo electrical effects creating electrical impulses during drying due to crystalline structures in the wood and several more which will not be discussed, although further complications arises due to them. Wood rivals if not champions the most complex composite dielectrics, is rich in anomalies and unexpected behavior. These anomalies and properties are crucial to understand why some measuring processes in prior art, when applied to wood, are irrelevant or non-functional and will be referred to in sequel.

Figure 1:
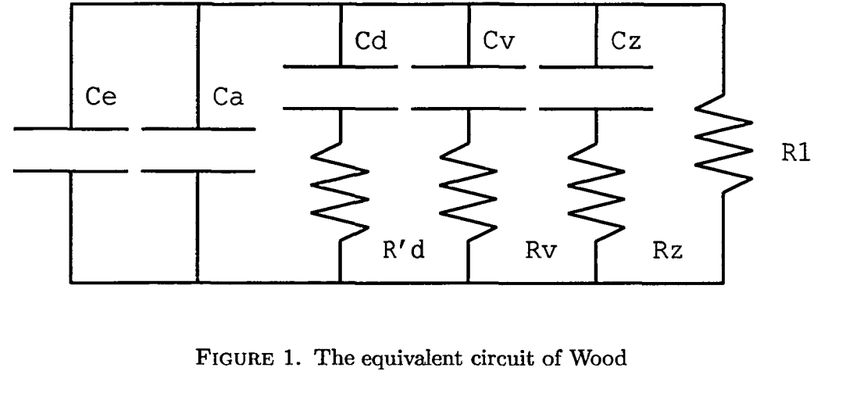
FIG. 1 is a circuit diagram of an equivalent circuit for the full dielectric model of wood.
Figure 2:
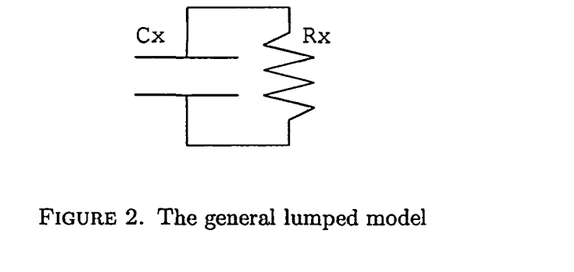
FIG. 2 is a circuit diagram of a simplified equivalent circuit assumed in the system of the invention.

Definition of Terms.
Moisture Content
Defined as the following percentage, (1)

$$M.C. = 100 \frac{M_w - M_d}{M_d} \quad (1)$$

where,
$M_w$=Mass off Wet sample
$M_d$=Mass of Bone-Dry Sample.
Free water
Water present in the trachea of the wood sample.
Bounded Water
Water chemically bounded to the cell walls of the wood sample.
Fibre Saturation Point (f.s.p.)
Wood is comprised of a solid cell-wall structures combined with hollow tubes which is either filled with water or air depending on the moisture content (M.C.) of the sample.
The f.s.p. is the maximum moisture content where all water is absent from the trachea and all the remaining water is chemically bounded to the cell-walls. The typical f.s.p. for softwoods such as Pinus is 30% M.C. For hardwoods, this is typically 40-50% M.C. This, however, varies from species to species according to density.
Wood drying installation
A wood drying installation is any construction or device in which wood can be dried, e.g., a kiln.
Material
The present invention can be applied to any dielectric material. In case of wood it includes both hard and soft woods, which can be in several states namely dimensional lumber, wood chips, veneer, saw dust or logs.
Correlation of Measurement with Moisture Content. Several correlations are possible:
Correlation of the moisture content with the dielectric constant $\in_r$. This manifests itself in capacitance measurements where capacitance is obtained from $\in_r$ by mans of the probe geometry.
Correlation of the moisture content with the Conductivity. These are mostly referred to as resistance type meters employing alternating or direct current.
Correlation of the moisture content with the loss-tangent (tan δ). These are referred to as loss-tangent measuring principles employing alternating current.
Dielectric Model of Wood as Medium.
It is well known from literature that the sensitivity of inductance to moisture content of wood is negligible. The dielectric for wood would then comprise of the various influences of dielectric constant and conductivity σ only.
The full dielectric model for wood is displayed in FIG. 1. All the different kinds of polarizations evident for wood are represented by the various capacitances. They are $C_e C_a C_d C_v$ and $C_z$, effected by electronic, ionic, dipole, interfacial, electrolytic, polarizations. $R_d$, $R_v$, $R_z$ and $R_1$ are the resistances resulting from energy losses at dipole, interfacial, electrolytic, and resistance related to the direct current, respectively. The model in FIG. 1 is for analytical purposes and a practical model used in determination of dielectric properties of wood for commercial systems is the Thevenin-Norton, lumped model as in FIG. 2 where the representative dielectric components are now the lumped values $C_x$ and $R_x$.
During discussion in sequel, it will be understood that the model as in FIG. 2 is used.
Definition of and Comparisons Between Resistive and Capacitive Sensors.
There are several other methods available such as "Neutron Probes" and "Infra Red" to name a few. These methods are undesirable for several reasons. It is of importance to focus on the two dielectric measurement principles namely "Capacitance" and "Conductivity" of the wood sample as is clear from. A serious concern regarding the use of the type of measurement in literature is now raised as it presents considerable confusion if not addressed.
It is obvious from that a measurement principle which claims to be a Capacitance meter must be able to single out and measure only the $C_x$ in FIG. 2 and be generally insensitive to changes in $R_x$.
Likewise, a measurement principle which claims to be a Resistance meter must be able to single out and measure only the $R_x$ in FIG. 2 and be generally insensitive to changes in $C_x$.
Then, for a measurement principle to claim to be a loss-tangent meter (tan δ) it must be clear that the meter combines the $R_x$ and $C_x$ components in such a way as to represent loss-tangent closely.
Any measurement principle unable to separate the components $R_x$ and $C_x$ in 2 will therefore be a non-linear convolution of dielectric properties and no fundamental information regarding $R_x$ and $C_x$ can be extracted. The output of such measurement is therefore some convoluted indication of the influences of both $R_x$ and $C_x$. This measurement type will be referred to a of type "convoluted" in sequel.
Measurement methods which can measure and identify $R_x$, $C_x$ and tan δ accurately and independently will be described as "True-measurements" in sequel.
Furthermore, if a single measurement principle can obtain all the separate dielectric properties at once and in real time, it will be called "real-time measurements" in sequel. The patent applications [E] and [N], essentially presents a real-time form of these quantities.
The present invention allows the use of a general impedance as a detector, opening up a method to use a cost-effective detector to measure at both high and low frequencies, using combinations of resistance, capacitance, and inductance.

In order to measure at high frequencies, it is necessary to keep probe wires as short as possible and interference at the minimum. The present invention approaches this by using the kiln as a co-axial cable to deliver both power and data in the closest proximity of the measuring device containing the detector. An example of employing the kiln as a co-axial cable is the measurement of the fiber saturation point. Further advantages of using a kiln as a co-axial cable is better reliability of the measurement system, because the use of multiple probe wires suspended from the kiln walls to the probes in the wood can be eliminated, on which wood often could fall and disable the system. Moreover, the installation of the measuring system is much simplified by not requiring the internal wiring, which can take up to two days of installation time by a contractor.

In comparison to the present invention, Venter et al. [N] uses a series resistance in combination with a dielectric model as an algorithm in order to obtain the components $R_x$, $C_x$ of the impedance $Z_x$ independently and simultaneously. The current invention does not use a series resistance, but a general impedance $Z_s$ which is not a single resistance $R_x$. Steele [H] does not disclose a detection circuit and is therefore not enabling a measurement method. Steele requires the detection circuit to be an oscilloscope, which by itself is insufficient, as a detection circuit is needed in conjunction thereof. Such a detection circuit, is e.g. a series resistor. Inclusion of such a series circuit would lead to the invention as disclosed in [N].

Logan [?] discloses a back-to-back matched transistor circuit of which one half-circuit measures moisture content of the wood while the other half-circuit measures a reference load where the reference load is a capacitance. The reactive load is not driven through an impedance as disclosed in the current application, but compared with a fixed capacitive reference. They are therefore not equivalent methods.

SUMMARY OF THE INVENTION

The present invention is directed to a wood drying installation comprising a wood drying kiln, a pair of electrodes, of which at least one is to be inserted into wood contained in said kiln, a predetermined impedance Zs or its Thevenin-Norton equivalent connected in a series circuit with said electrodes, wherein the impedance Zs is not a pure resistance, an AC voltage source connected to apply an AC voltage across said series circuit, a phase detecting device connected to said series circuit operable to generate a signal representing the phase angle between AC voltages applied to different parts of said series circuit, and a processor connected to receive said signal and operable to determine a value corresponding to at least one of an independent capacitive component Cx, an independent resistive component Rx and independent inductive component Lx of the impedance Zx between said electrodes in accordance with a predetermined arithmetic algorithm relating said value to said phase angle, and V1 and V2.

In one aspect of the present invention, the Zs is a capacitance Cs or an inductance Ls. In another aspect, Zs is a combination of at least two components selected from Rs, Cs, and Ls.

In yet another aspect of the invention, the voltages are applied to different parts of said series circuit comprise a voltage applied across said electrodes and the voltage applied across said series circuit.

In another aspect, the arithmetic algorithm expresses said value as a function of said phase angle, said voltage, and said series impedance Zs.

In a still further aspect, said processor determines the impedance Zx.

In yet another aspect, said phase detecting circuit converts said AC voltages applied to different parts of said series circuit to square wave voltages and an exclusive or circuit receiving said square wave voltages. Moreover, said circuit further may comprise an RMS-to-DC converter connected to receive the output of said exclusive or circuit.

In another aspect, said device is an FPGA, DSP, microcontroller or a discrete circuit.

In the wood drying installation according to the present invention, the data transmission may be performed by using the kiln as a coaxial cable, wherein the metal kiln walls, doors and grounded floor comprises the outer coaxial conductor (shield) relative to an axial central conductor. The central conductor can be a metallic rail track electrically not at short-circuit with the shield. Furthermore, the central conductor can be any axial conductor electrically not at short circuit with the shield. In one aspect, the kiln as coaxial cable is used for data and power transmission.

The present invention also relates to a method of measuring the moisture content of a stack of wood in a kiln comprising placing at least one of a pair of electrodes in said stack of wood in said kiln, connecting a known series impedance Zs in series with said pair of electrodes, applying a AC voltage across said series circuit, detecting AC voltages applied to different parts of said series circuit, determining a phase angle between said AC voltages applied to different parts of said circuit, and calculating a value corresponding to at least one of an independent capacitive component Cx, an independent resistive component Rx and independent inductive component Lx of the impedance Zx between said electrodes in accordance with a predetermined arithmetic algorithm relating said value to said phase angle and the voltages V1 and V2.

In one aspect of the method, said voltages applied to parts of said series circuit comprise the voltage applied across said series circuit and a voltage applied across said electrodes.

In a further aspect, said independent capacitive component is calculated according to the equation $$C_x = \left| \frac{\sin(\phi)\cos(\tau)V_1 + \sin(\tau)\cos(\phi)V_1 - V_2\sin(\tau)}{U_w V_2} \right| \quad (2)$$

In yet another aspect of the method, said independent resistive component is calculated according to the equation $$R_x = \left| \frac{UV_2}{-\cos(\phi)\cos(\tau)V_1 + V_2\cos(\tau) + \sin(\phi)\sin(\tau)V_1} \right| \quad (3)$$

In yet another aspect, said independent inductive component is calculated according to the equation $$L_x = \left| \frac{UV_2}{\omega[\sin(\phi)\cos(\tau)V_1 + \sin(\tau)\cos(\phi)V_1 - V_2\sin(\tau)]} \right| \quad (4)$$

Furthermore, in another aspect, the loss tangent tan δ is calculated according to the equation $$\tan\delta = \frac{1}{\omega R_x C_x} \quad (5)$$

In a further aspect, the moisture content of the wood is above fiber saturation point of the wood.

In yet another aspect of the method, the fiber saturation point of the wood is determined by measuring the loss tangent of the wood and determining the point where the loss-tangent equals zero, the latter which corresponds to the fiber saturation point.

The present invention is further directed to a system for measuring the reactive impedance of a dielectric material between a pair of electrodes, wherein said system comprises a known impedance $Z_s$ connected in a series circuit with said electrodes, an AC voltage source connected to apply an AC voltage across said series circuit, a phase detecting circuit connected to said series circuit operable to generate a signal representing a phase angle between AC voltages applied to different parts of said series circuit, and a processor connected to receive said signal and operable to determine a value corresponding to at least one of an independent capacitive, independent resistive and independent inductive component of said reactive impedance in accordance with a predetermined arithmetic algorithm which expresses said value as a function of said phase angle, said voltages and said series impedance.

In one aspect of the system, the voltages applied to different parts of said series circuit comprise a voltage applied across said electrodes and the voltage applied across said series circuit.

In another aspect of the system, said phase detecting circuit converts said AC voltages applied to different parts of said series circuit to square wave voltages and an XOR circuit receiving said square wave voltages. Said circuit further comprises an RMS-to-DC converter connected to receive the output of said exclusive or circuit. Moreover, in another aspect, said AC voltage source provides a sinusoidal voltage.

In another aspect, the present invention relates to a method of measuring the reactive impedance of a material comprising placing a pair of electrodes in said material, connecting a known impedance $Z_s$ in series with said pair of electrodes, applying a AC voltage across said series circuit, detecting AC voltages applied to different parts of said series circuit, determining a phase angle between said AC voltages applied to different parts of said circuit, and calculating a value corresponding to at least one of an independent capacitive component, an independent inductive component and an independent resistive component of the reactive impedance between said electrodes in accordance with a predetermined arithmetic algorithm which expresses said value as a function of said phase angle, said voltages and said series impedance.

In one aspect of the method, said voltages applied to parts of said series circuit comprise the voltage applied across said series circuit and a voltage applied across said electrodes. In another aspect, at least one of said voltages comprises a sinusoidal voltage.

In a further aspect of the method, said independent capacitive component is calculated according to the equation $$C_x = \left| \frac{\sin(\phi)\cos(\tau)V_1 + \sin(\tau)\cos(\phi)V_1 - V_2\sin(\tau)}{U\omega V_2} \right| \quad (6)$$

In yet a further aspect, said independent resistive component is calculated according to the equation $$R_x = \left| \frac{UV_2}{-\cos(\phi)\cos(\tau)V_1 + V_2\cos(\tau) + \sin(\phi)\sin(\tau)V_1} \right| \quad (7)$$

Furthermore, said independent inductive component is calculated according to the equation $$L_x = \left| \frac{UV_2}{\omega[\sin(\phi)\cos(\tau)V_1 + \sin(\tau)\cos(\phi)V_1 - V_2\sin(\tau)]} \right| \quad (8)$$

In another aspect, the loss tangent tan δ is calculated according to the equation $$\tan\delta = \frac{1}{\omega R_x C_x} \quad (9)$$

The present invention is also directed to a wood drying installation comprising a kiln as coaxial cable element for a data transmission, wherein metal walls and doors of the kiln grounded to the soil comprise the outer coaxial conductor (shield) relative to a substantially isolated axial central conductor.

In one aspect of the wood drying installation, the central conductor is a metalic rail track electrically not at short-circuit with the shield. In another aspect, the central conductor can be any axial conductor electrically not at short circuit with the shield.

In a further aspect, the kiln as coaxial cable element is used for data and power transmission.

In yet another aspect, the kiln as coaxial cable element is connected to a measurement device, wherein a preferred measurement device is a dielectric moisture meter.

The present invention further relates to a method for determining the fiber saturation point of wood comprising measuring the loss tangent of the wood and determining the point where the time derivative of the loss-tangent equals zero, the latter which corresponds to the fiber saturation point of the wood.

In one aspect, the method for determining the fiber saturation point of wood also includes determining the density of wood by measuring the fiber saturation point, and obtaining the density from the well known relationships between density of wood and f.s.p.

DETAILED DESCRIPTION OF THE INVENTION

The particulars herein are by way of example and for purpose of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

There are three preferred but not exhaustive embodiments of the present invention.

First Embodiment

Figure 7:
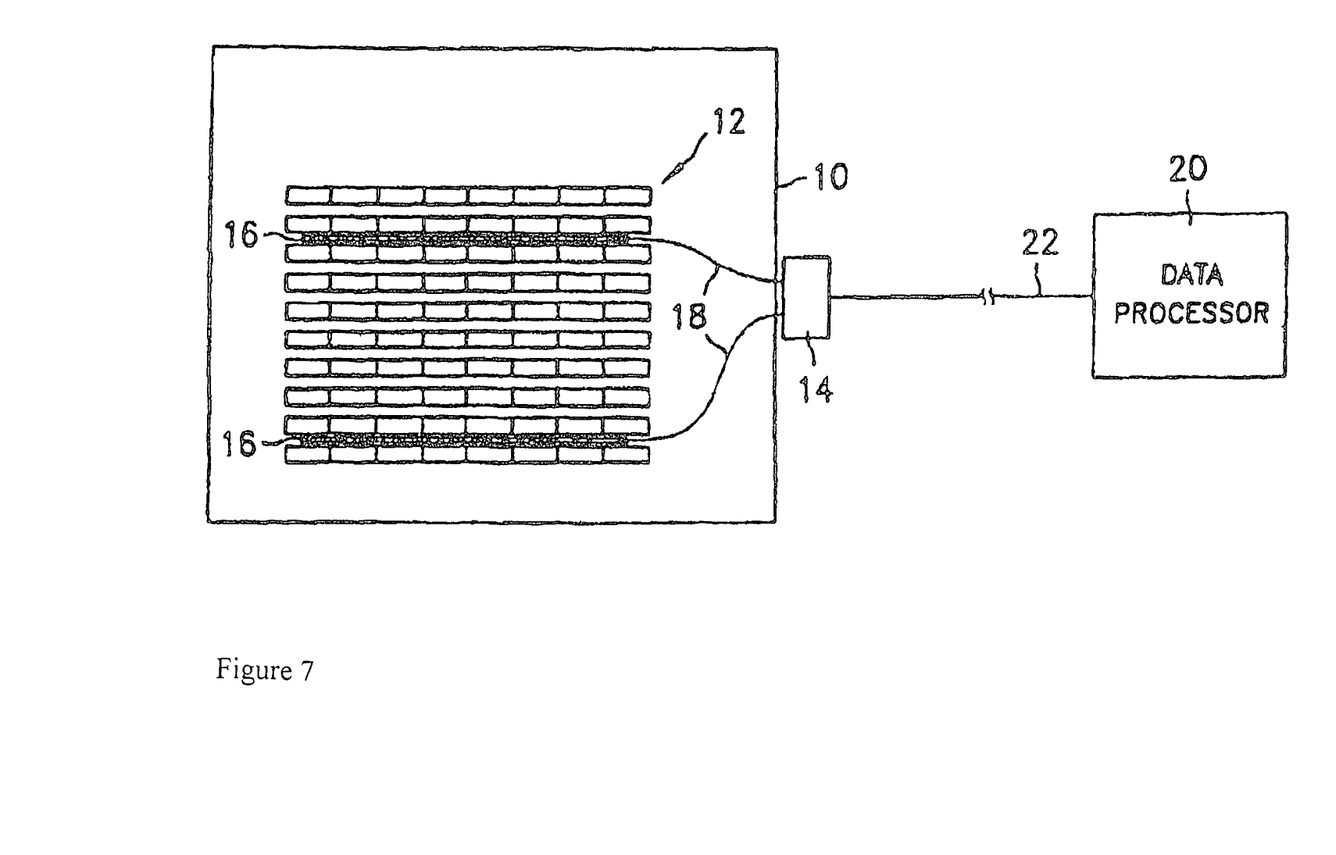
FIG. 7 is an end view of a stack of timber, in a wood drying kiln provided with measuring means in accordance with the invention.
Figure 8:
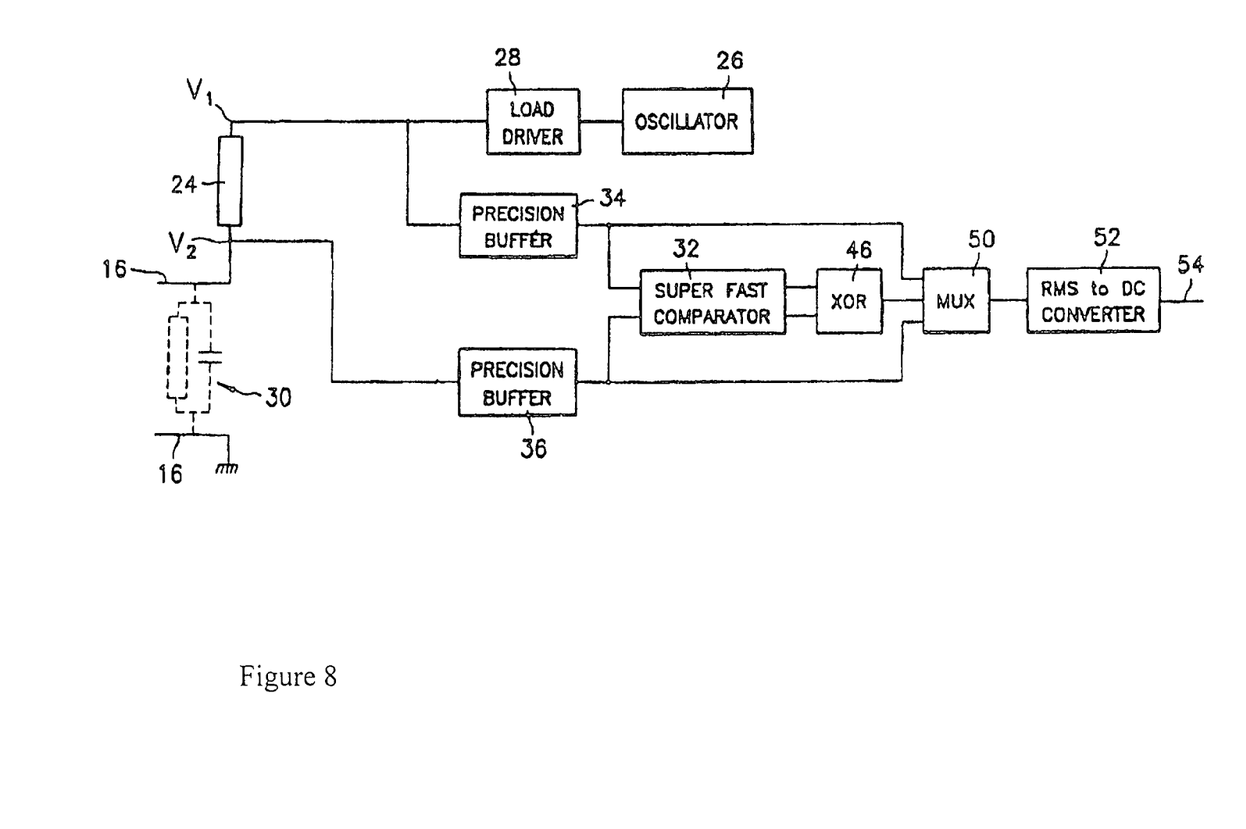
FIG. 8 is a block diagram of a measuring means.
Figure 9:
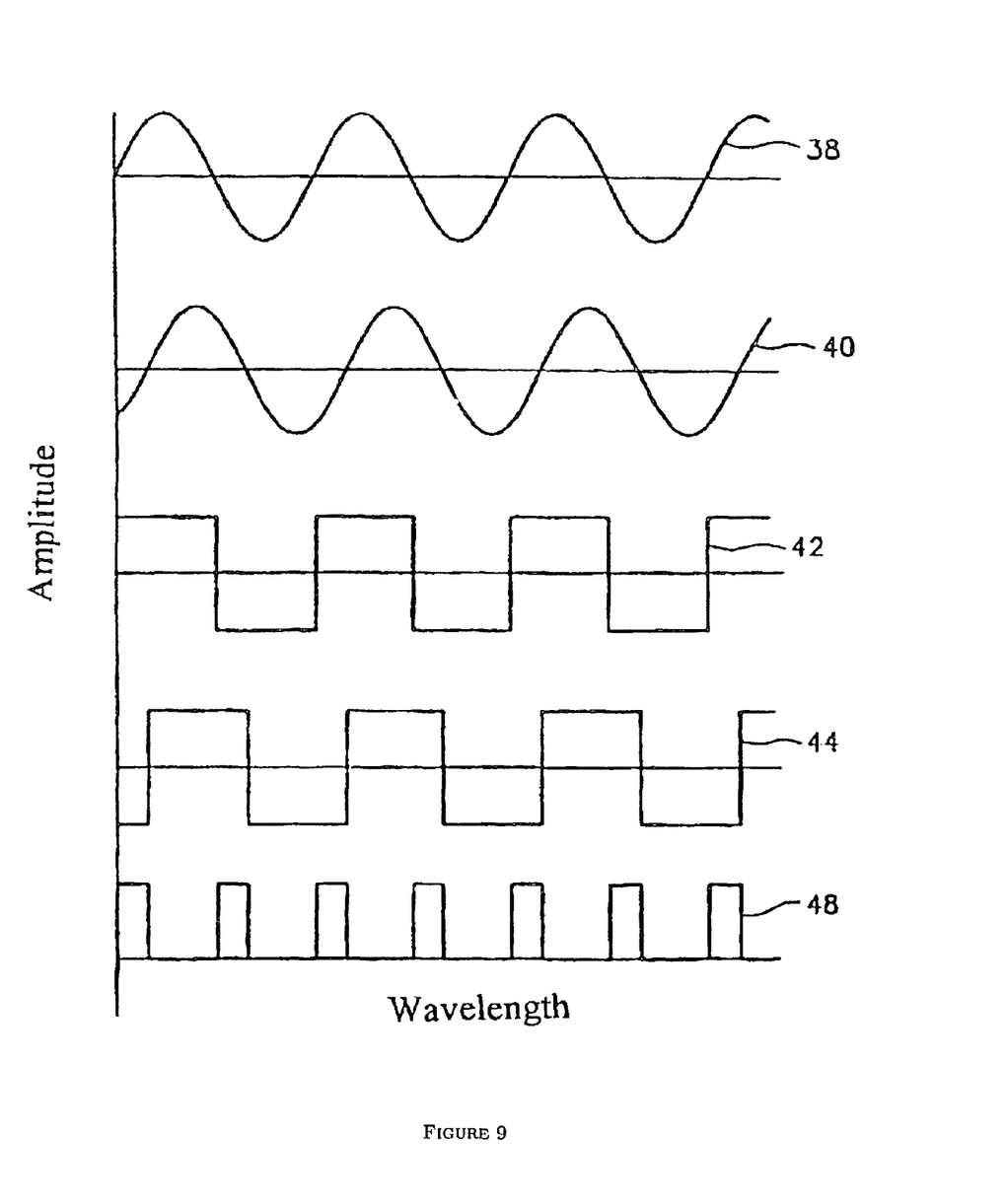
FIG. 9 shows certain voltage waveforms.
Figure 10:
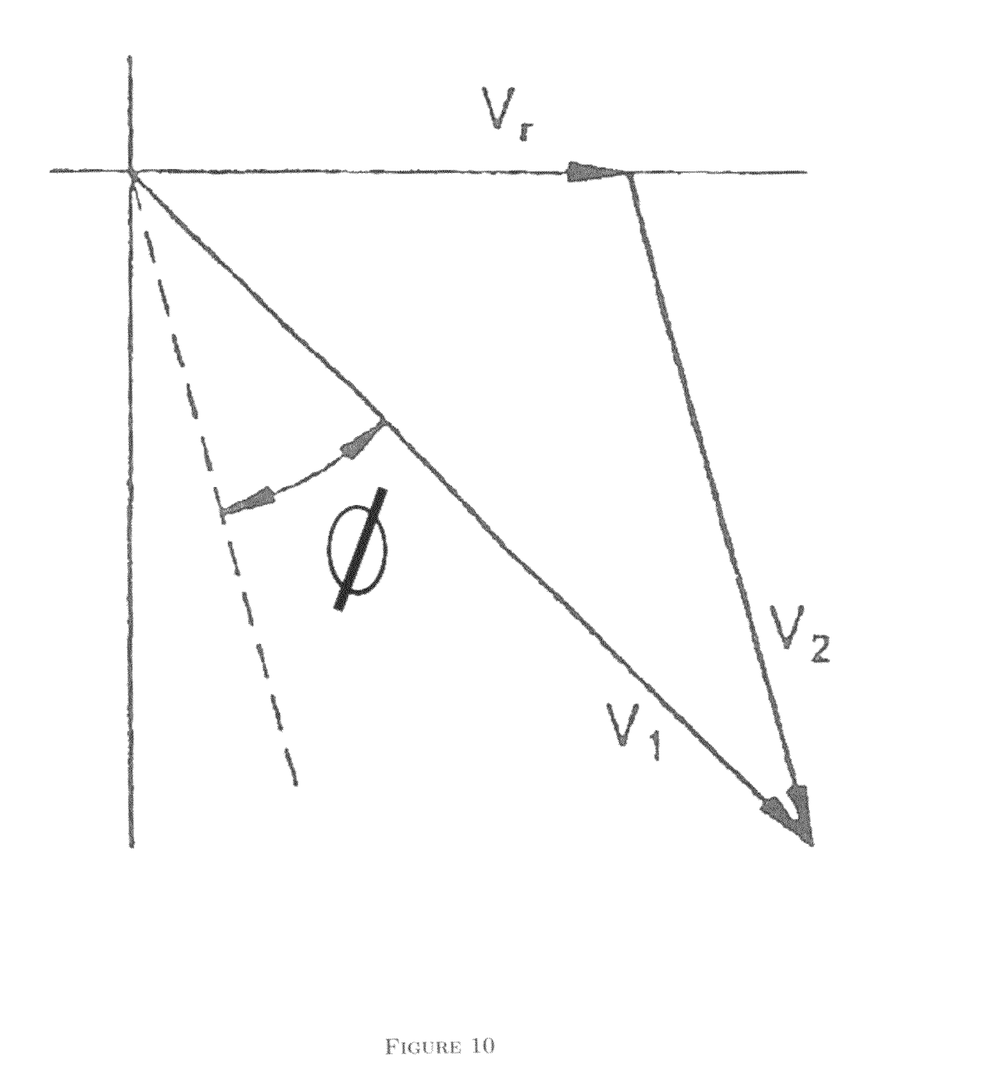
FIG. 10 is a phasor diagram of the voltages.

Referring to FIG. 7 and, FIG. 8 in more detail, reference numeral 10 indicates a wood drying kiln in which there is a stack timber 12. The timber 12 is arranged in layers which are spaced by means of spacers. The environment inside the kiln is controlled to facilitate drying with minimum defect. To determine the dielectric properties of the wood accurately, the kiln is provided with a measuring means comprising of an electronics module 14 outside or inside the kiln, a pair of electrodes 16 inside the kiln coupled to the module 14 by means of electric conductors 18, and a remote data processor 20 which is connected to the electronics module 14 by means of a data link 22. Where there are a number of kilns 10, each with it's own electronics module 14, the various electronic modules may all be connected to the same data processor 20. The electrodes 16 are in the form of metal plates and are simply inserted into the spaces between layers in the stack 12. It is an important feature of the invention that the electrodes 16 do not need to be cleaned prior to insertion into the stack, as operation of the apparatus is not affected by the degree of physical contact with the timber, the size and exact separation of the electrodes are also not important since if the size of the electrodes are changed, then a factor in the data processor can be adjusted to compensate. The electronics module 14 serves to measure the values which are required to determine the capacitance, resistance and inductance of the complex impedance between the electrodes 16. The electronics module further comprises of a very fast comparator 32, which is connected via a precision buffer 36 to one of the electrodes, the other electrode being connected to instrumentation ground. Both electrodes 16 are electrically isolated from the kiln. The waveform of the applied voltage (i.e. the output of the driver 28) is indicated at 38, whereas the waveform of the voltage across the electrodes 16 (i.e. after the general series impedance $Z_s$, 24) is indicated by reference 40 in FIG. 7. In FIG. 10, the applied voltage 38 is indicated by the phasor $V_1$ and the voltage across the electrodes by phasor $V_2$. Because the impedance 30 is complex, there is a phase difference between the voltages $V_1$ and $V_2$, this being indicated by the angle $\phi$. $V_r$ is the voltage ac-cross the series impedance element $Z_s$. The comparator 32 serves to convert the sinusoidal voltage 38 and 40 to square wave voltages 42 and 44 respectively. the electronics module 14 further comprises an exclusive-or (XOR) circuit 46 whose output is indicated at 48. The peak and the RMS value of the output 48 varies in proportion to the phase difference between the voltages 38 and 40. The outputs of the buffers 34 and 36 and the output of the XOR circuit 46 are fed into a multiplexer 50, which is used to select one of $V_1$, $V_2$ or phase angle $\phi$ to be measured by the RMStopC converter 52. Output 54 of the RMS-to-DC converter 52 is relayed to the data processor 20, via the data link 22.

Obtaining the Electrical Components of the Dielectric.

The dielectric components of wood is that of a resistance $R_x$, capacitance $C_x$ in parallel as in FIG. 2. Wood has no inductance, but the scope of the invention also includes the case of an inductance $L_x$ in parallel with $R_x$ and $C_x$ for dielectric applications with inductive dielectrics. In the event that the complex impedance includes an inductance ($L_x$) in parallel with $C_x$, both $C_x$ and $L_x$ can be obtained independently by measuring the complex impedance $Z_x$ at two different excitation frequencies. It is important to note that if $Z_x$ comprises of either $R_x$ and $C_x$ in parallel or $R_x$ and $L_x$ in parallel, then one excitation frequency is sufficient to determine both the components in parallel at the same time with one measurement. Two frequencies are only necessary for the case of $Z_x$ containing both a $C_x$ and a $L_x$ component.

The capacitive and resistive load ($Z_x$), as depicted in FIG. 2, is obtained rigorously by means of the following procedure. Element "30" in the drawing FIG. 8 will be referred to as $Z_x$ in sequel, meaning the parallel combination of the resistive and capacitive properties of the wood sample.

The impedance $Z_x$ (30) is driven through the Impedance $Z_s$ (24) and the voltage $V_2$ is measured across the load. The principle measurement is then the comparison between the applied voltage $V_1$ and the load voltage $V_2$ which also involves a phase detection.

In what follows we do not include calculations for the case of $Z_x$ containing an inductance. As will be shown, that can be obtained by a simple correspondence rule between $C_x$ and $L_x$ to obtain the equations for $L_x$.

It is now shown how to express the impedance in terms of the dielectric elements $C_x$ and $R_x$ and the angular frequency $\omega$.

The impedance of the dielectric medium can be obtained in terms of $R_x$ and $C_x$ as $$z_x = \frac{R_x Z_c}{Z_c + R_x} \tag{10}$$

Expanding the equation by substituting with $$z_x = \frac{1}{j\omega C_x}$$

expanding into real and imaginary parts the impedance becomes, $$Z_x = \frac{R_x}{1 + \omega^2 C_x^2 R_x^2} - j \frac{R_x^2 C_x \omega}{1 + \omega^2 C_x^2 R_x^2} \tag{11}$$

Rewriting this in terms of magnitude and angular using the Euler description yields, $$\|Z_x\| e^{j\theta} \tag{12}$$

where $$\|Z_x\| = \frac{R_x}{(1 + \omega^2 C_x^2 R_x^2)} \sqrt{1 + R_x^2 C_x^2 \omega^2} \quad (13)$$

and (14)

$$\theta = \arctan(-\omega R_x C_x). \quad (15)$$

It is now shown how to express the impedance $Z_x$ in terms of the voltages $\overline{V}_1$, $\overline{V}_2$ and a series impedance $Z_s$ It is a trivial exercise to obtain, $$Z_x = \frac{Z_s \overline{V}_2}{\overline{V}_1 - \overline{V}_2} \quad (16)$$

Since $\overline{V}_1$ is the reference voltage (Applied Wave) the phase angle is zero. The load wave obtained at $V_2$ will display some amplitude decrease due to the dielectric loss of the medium (wood) and also display a phase difference $\phi$ due to the 80|1 polarization of the H$_2$O molecules and the cell-wall structure in the presence of the electromagnetic field.
Therefore define, $$\overline{V}_1 = V_1, \overline{V}_2 = V_2 e^{j\phi} \text{ and } Z_s = U e^{j\tau}.$$

By substitution of 17 into 16 and after expanding into real and complex parts and finally rewriting in Euler form, $Z_x = \|Z_x\| e_{j(\phi+\delta+\tau)}$, the following is obtained.

$$|Z_x| = \frac{UV_2}{\sqrt{V_1^2 - 2V_1 V_2 \cos(\phi) + V_2^2 \ast \cos(\phi)^2) + V_2^2 \sin(\phi)^2}} \quad (18)$$

where $$\delta = \arctan \frac{V_2 \sin\phi}{V_1 - V_2 \cos\phi} + \phi + \tau \quad (19)$$

Since the impedances 18 and 12 are the same in magnitude and phase angle it follows that, $$\theta = \phi + \delta + 2k\pi \text{(multiple solutions irrelevant, assume } k=0\text{)}$$
and (20)

$$\frac{UV_2}{\sqrt{V_1^2 + V_2^2 \cos(\phi)^2 - 2V_1 V_2 \cos\phi + V_2^2 \sin(\phi)^2}} = \frac{R_x}{\sqrt{(1 + \omega^2 C_x^2 R_x^2)}} \quad (21)$$

After some extended simplification it is found that $$R_x = \left| \frac{UV_2}{-\cos(\phi)\cos(\tau)V_1 + V_2 \cos(\tau) + \sin(\phi)\sin(\tau)V_1} \right| \quad (22)$$

$$C_x = \left| \frac{\sin(\phi)\cos(\tau)V_1 + \sin(\tau)\cos(\phi)V_1 - V_2 \sin(\tau)}{U\omega V_2} \right| \quad (23)$$

where the absolute values of $R_x$ and $C_x$ are taken as they are generally defined as positive values.

Although wood has negligible inductance, we can obtain an equation for inductance $L_x$, for any material having inductance by the impedance correspondence $$Cx \leftrightarrow -\frac{1}{\omega^2 L_x}$$

$$L_x = \left| \frac{UV_2}{\omega[\sin(\phi)\cos(\tau)V_1 + \sin(\tau)\cos(\phi)V_1 - V_2 \sin(\tau)]} \right| \quad (24)$$

The following improvements due to this method will be obvious to anyone skilled in the art.

Measurement of $C_x$, $R_x$ and $L_x$ Independently

It is clear form and equations 22, 23 and 24 that by only measuring the magnitudes $V_1$, $V_2$ and the phase angle between these two sinusoids, that the capacitance $C_x$ and the resistance $R_x$ or the resistance and inductance $L_x$ can be obtained simultaneously within the resolution of the measurement. It must be stressed that $C_x$ (respectively $L_x$) is obtained independently form $R_x$ and that variations of one do not influence the other. If an impedance $Z_x$ is comprised of all three of $R_x$, $L_x$ and $C_x$, then all can be determined by using data from two frequencies.

Measurement of $C_x$ and $R_x$ and Tan $\delta$ Instantaneously

Both $C_x$ and $R_x$ can be obtained simultaneously by evaluating the equations 22 and 23 by only measuring $V_1$, $V_2$ and the phase angle ($\phi$) once. Furthermore the loss-tangent can be constructed from $C_x$ and $R_x$ by the equation tan $$\delta = \frac{2}{\omega R_x C_x}$$

, where $R_x$ and $C_x$ is described by 23 and 22.

Rejection of oscillator amplitude variations ($V_1$) of the source.

The signal voltage $V_1$ and the voltage across the load $Z_x$ is related as $$V_2 = \left\| \frac{Z_x}{Z_s + Z_x} \right\| V_1 \quad (25)$$

Any variation in $V_1$ will also create a proportional variation in $V_2$. Therefore, $$\frac{V_1}{V_2}$$

would be largely constant for any power supply variation, it is clear to see that the result of the determination of $Z_x$ and therefore also $L_x$, $C_x$ and $R_x$ in 24,22 and 23 will be invariant under any variations and as a consequence also tan $\delta$ as it is constructed uniquely from $C_x$ and $R_x$.

Transparent and Simple Cancelling of Probe Wire Dielectrics.

Since the measurement principle can detect $R_x$ and $C_x$ independently, the resistance and capacitance of the probe wiring can be established once and accurately. Since Capacitances adds in parallel, the probe wire capacitance can simply be subtracted from the capacitance measured with a load attached in order to obtain the capacitance of the wood sample as $C_L=C_T-C_C$, where $C_L$, $C_T$ and $C_C$ are the load, total and cable capacitances respectively. This is not the case with prior art. Resistance of probe wiring is cancelled by choosing relatively thick conductors or too be more accurate measure the short circuit resistance and obtain the load resistance form $$\frac{1}{R_L} = \frac{1}{R_T} - \frac{1}{R_C},$$

where $R_T$ is the total resistance measured, $R_L$ is the load resistance and $R_C$ is the cable resistance. The instantaneous measurement of Capacitance and Resistance by the method of this invention therefore easily systematically and clearly removes the cable dielectric properties in order to obtain the dielectric properties of the medium independent from cable dielectric influences. A similar procedure can be followed to cancel the wire inductance in the case that $Z_x$ contains an additional inductance $L_x$ in addition to $C_x$ and $R_x$ by taking the measurements at two different frequencies. For the case of $Z_x$ comprising of either $R_x$ and $L_x$ or $R_x$ and $C_x$, measurement at only one frequency is necessary.

The above described system measures the capacitance, resistance and inductance of a reactive load represented by a stack of wood produced between two plates as probes. In accordance with the invention, the reactive load is connected in a series circuit with a known impedance and the voltage across the reactive load is measured as well as the excitation voltage feeding into the series impedance. The phase angle φ between the two voltages is determined and from the values of the known impedance, the magnitudes of the voltages and the phase-angle between them, the capacitance, resistance and inductance of the reactive load are determined according to equations expressing the capacitance, resistance and inductance in terms of the known voltages, known impedance and known phase-angle. It is appreciated that the equivalent Thevenin-Norton descriptions of both the known and unknown impedances can also be used to obtain the same result and that such descriptions are equivalent. A benefit of using a capacitance or a capacitance in parallel with a resistance as the impedance element $Z_s$ is that at higher frequencies $Z_s$ decreases in value. This makes operation at high excitation frequencies possible. It also makes it possible to construct a $Z_s$ which has more constant magnitude with varying frequency. $Z_s$ as resistance is ideal for working at low excitation frequencies where $Z_s$ as capacitance is better for higher frequencies.

Second Embodiment

Using a Kiln as a Co-axial cable.

One of the major problems facing installation of dielectric moisture meters in a lumber drying kiln, is all the probe wiring and feed through cables necessary to measure the moisture content of various stacks of wood inside the kiln. Normally systems will employ probe wire and or power cables or coaxial cable running on electrical isolators terminated in a service point where connections to the plates in the wood can be made. This involves long lengths of cabling inside the kiln which creates maintenance and expensive installation procedures.

In order to solve these problems, the method described in this invention, involves using the Kiln itself as a coaxial cable element, thereby using the kiln as co-axial cable to suppress common mode noise during data transmission due to the well-known inherent properties of a co-axial cable element. The same co-axial cable arrangement can be used to transmit data and power to instrumentation inside the kiln.

Figure 5:
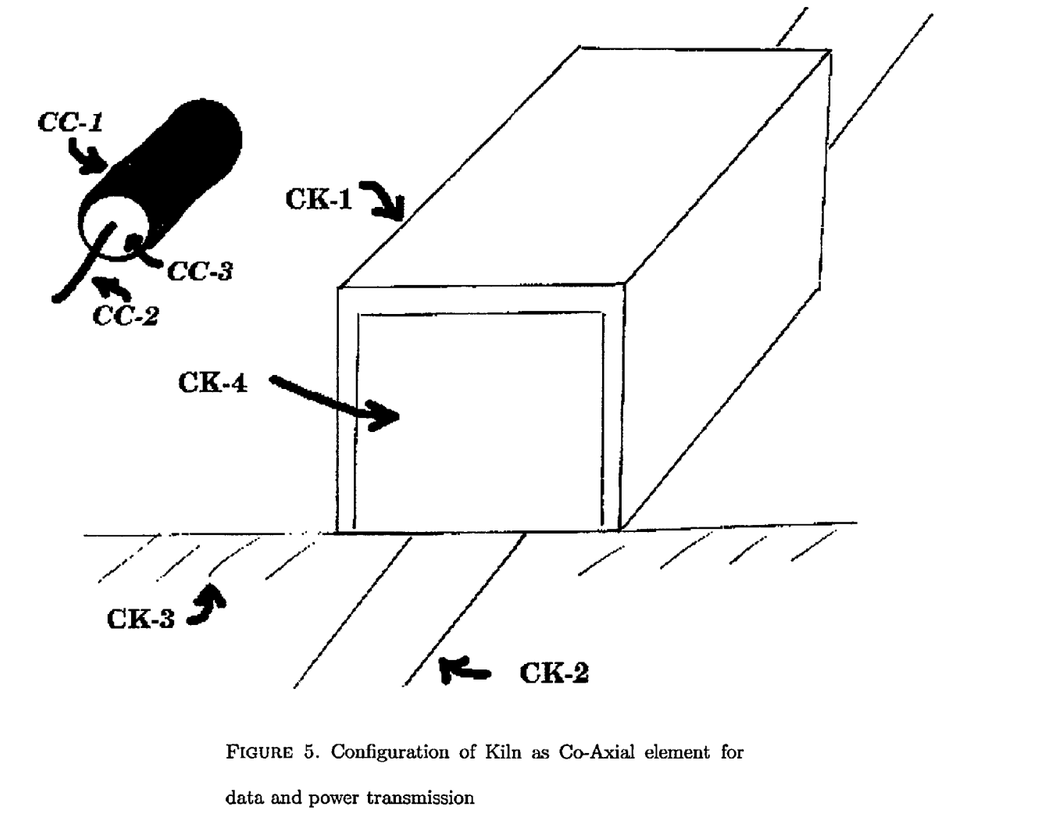
FIG. 5 is a view of the configuration of a Kiln as a Co-Axial element for data and power transmission
Figure 6:
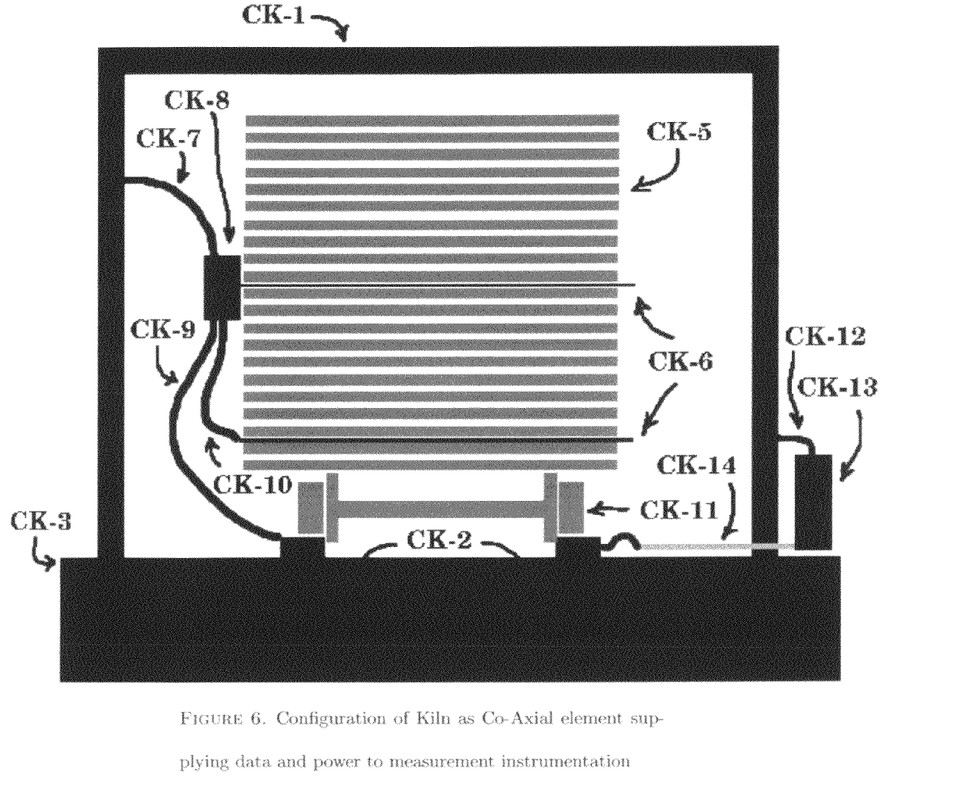
FIG. 6 is a cross-sectional view of a kiln Kiln configured as Co-Axial element supplying data and power to measurement instrumentation.

FIG. 5 and FIG. 6 displays the configuration as discussed above. In FIG. 5 a classical co-axial cable is displayed, where the tubular axial metal shield (CC-1) wraps around a dielectric (CC-3) usually made of e.g. PTFE or similar. The center of the dielectric is pierced by a conductor (cc-2) which is co-axial to the shield CC-1. A typical metal drying kiln consists of a frame (CK-1) cladded by e.g. Aluminum closed on both side by Aluminum doors (CK-4), forming a square cross-sectional cylinder. The metal kiln body is grounded by means of a 2-3 m metal grounding rod or obtains it's ground from the electrical motor grounding grid. The soil on which the kiln is built therefore completes a sufficiently conductive bottom plane of typically 5-20. This conductive layer competes the shield to form a closed cylinder. This shield formed by (CK-1) and the soil, has it's analog in the classical co-axial cable as (CC-1).

Most high volume metal drying kilns are equipped with rails (CK-2) resembling train-tracks for the loaded stacks to be pushed into the kiln. These metal tracks are fastened onto a continuous concrete slab (CK-3) running through the kiln. The concrete slab is a very good isolator, isolating the rails (CK-2) from the soil. This metal track naturally becomes the isolated central conductor of the coaxial cable with analog (CC-2) of the classical co-axial cable).

As a result, the kiln is therefore configured as a coaxial cable element of which the dielectric in the kiln, equivalent to (CC-3), is a combination of air and wood.

FIG. 6 shows a cross section of a loaded kiln with the measurement instrumentation showed as connected to the stack of wood (CK-5) to measure for example, the dielectric properties of the wood between the plates (CK-6). In more detail, a measuring device (CK-8) which can be any dielectric moisture meter. The measuring device is connected directly to an upper metal plate extending through the wood. The measuring device is further connected to the remaining bottom plate of the plate pair (CK-6) with a conductor (CK-10). The measuring device obtains data communication and power supply through, one conductor connected to the rail tracks (CK-2) or the metal cart (CK-11), while another conductor (CK-7) is connected to the metal kiln wall (CK-1). The measuring device is now connected to a coaxial cable element. Data and Power are supplied through cables (CK-14) connecting to the rails (CK-11) and cable (CK-12) connecting to the kiln wall (CK-1). A Power and Data transmission system (CK-13) connected to cables (CK-12) and (CK-14) is mounted inside or on the outside of the kiln. The data transmission protocol ideally should be a differential protocol such as RS-422/485 or similar. The use of a differential protocol combined with the kiln as coaxial cable element ensures reasonably high data rates with low failure rates. The Power and data transmission system (CK-13) is then connected by either a data cable or by RF parabolic dish to the processing unit in the control room displaying the measured dielectric properties correlated to e.g. moisture content and Fiber saturation point.

Third Embodiment

Using the Loss Tangent as a detector for Fiber Saturation Point (F.S.P.)

Fiber saturation point detection is a crucial property to detect in wood-drying. It will now be described how Fiber Saturation Point Detection employing the Loss-Tangent can present a unambiguous clear detection of F.S.P. Traditional methods of measuring F.S.P. involve Direct Current conductivity measurements and determining when the conductivity desaturates and starts to decrease as salts starts to deposit on the cell-walls as free water is lost and the remainder of water when the wood is below F.S.P. becomes chemically bounded. The weakness of this method lies in that it can take considerable amounts of time to establish that the conductivity is dropping out of saturation.

In the present invention, it has been found that determining the F.S.P. via the loss tangent is a superior method in comparison to the to conductivity method for detecting F.S.P. The Loss-Tangent of a dielectric medium against moisture content resembles the shape of a "Bell-curve", whereby the maximum of the bell curve occurs at F.S.P. In the case of wood as medium, the F.S.P. is accurately dependent on the density of the wood which in turn influences the amount of free water in the wood. The higher the density, naturally the fiber saturation point occurs at higher moisture contents. This is conclusive, since higher density causes less space for free water in a fixed volume of wood as medium.

The Bell curve shape of the Loss-Tangent, creates a unique and easy way to determine the F.S.P. compared to guessing when conductivity is out of saturation. The method of the present invention only requires to obtain the condition $$\frac{\partial_{tan}(\delta)}{\partial t} = 0$$

of the Loss-Tangent curve, which corresponds to the F.S.P.

Figure 3:
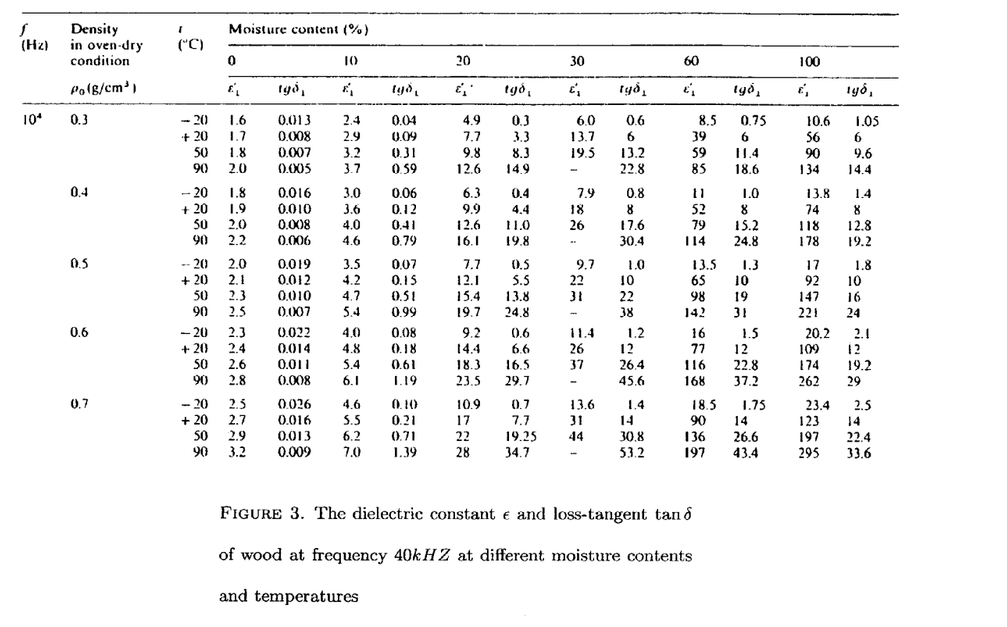
FIG. 3 is the dielectric constant $\in$ and loss-tangent tan δ of wood at frequency 40 kHZ at different moisture contents and temperatures.

The Table shown in FIG. 3, contains data for the loss-tangent tan δ, at fixed frequency, for several wood-densities and temperatures. If plotting the loss-tangent tan δ against moisture content at any given temperature for different densities, it can be seen that the higher the density the higher the moisture content where $$F.S.P\left(\frac{\partial_{tan}(\delta)}{\partial t} = 0\right)$$

occurs. For example, F.S.P. occurs at about 30% at density 0.5, temperature 90° C. and an excitation frequency of 10 kHz. The data shown in this table are not high resolution but sufficient to demonstrate the method.

Another benefit of detecting F.S.P via the loss-tangent is, that the moisture content of the material does not need to be known at all. Therefore, no calibration is necessary. The condition $$\frac{\partial_{tan}(\delta)}{\partial t} = 0$$

tells exactly when F.S.P occurs, independent of any knowledge of the moisture content.

Figure 4:
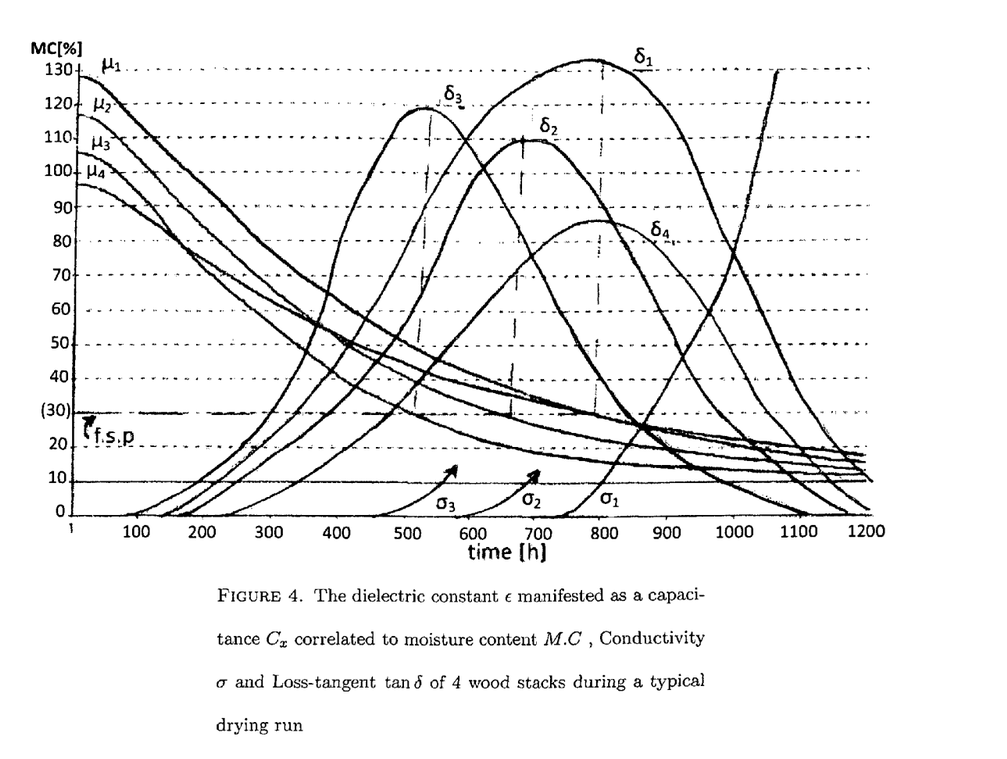
FIG. 4 contains curves showing the variation of the loss tangent and the moisture content ($C_x$) of wood vs. time. It further shows F.S.P (30% for pinus wood species) at the turning points of the loss-tangent, the related conductivity and related capacitance for a drying run. Note that e.g. $\mu_1$, $\sigma_1$ and $\delta_1$ are measured on the same dielectric sample no. 1 (which in this case is wood) versus time. In this case σ is displayed in compacted and bounded form $e^{-\sigma}$, which scales σ between the interval [0 . . . 1]. The compacted form is simply referred to as σ on the graph.

The data in FIG. 3 is relatively low resolution. When a high resolution model is used to determine $R_x$ and $C_x$ to in turn determine the loss-tangent tan δ=

$$\frac{1}{\omega R_x C_x},$$

a high resolution detection of F.S.P. by means of $\delta_1, \delta_2, \delta_3, \delta_4$, results in something similar as depicted in the graph FIG. 4 where $C_x$ (correlated with moisture content) $\mu_1, \mu_2, \mu_3, \mu_4$, $e^{-\sigma_x}$ and tan δ is plotted.

REFERENCES

[A] Ted et al U.S. Pat. No. 4,570,116, Feb. 11, 1986.
[B] Lundström U.S. Pat. No. 3,252,086 Jul. 16, 1962.
[C] Torgovnikov, G. I. Dielectric Properties of Wood, Springer Verlag, 1993, ISBN 3-540-55394, ISBN 0-387-55394.
[D] Spiegel M. R. Advanced Mathematics, Mc Graw Hill 1971.
[E] Venter, L R Viljoen, JPS Method of Determining the Dielectric Properties of Wood, and Means for use in such Method.
[F] Skaar C, 1948 The dielectric properties of wood at several radio frequencies. NY State Coll For, Syracuse, N.Y., Tech Publ 69
[G] Bechtel F. K. et al. Nov. 20, 1990. U.S. Pat. No. 4,972, 154.
[H] Preikschat F. K. Apparatus and method for providing . . . U.S. Pat. No. 4,174,498. Nov. 13, 1997.
[I] Preikschat F. K. Elctrode for an Impedance measuring . . . U.S. Pat. No. 4,107,599. Aug. 15, 1978.
[J] Vogel R. F. Means for measuring Loss-Tangent . . . U.S. Pat. No. 3,778,707. Dec. 11, 1973.
[K] Walsh J. E. Soil Moisture Sensor . . . U.S. Pat. No. 4,540,936. Sep. 10, 1985.
[L] Wagner D. W. Moisture Detector. U.S. Pat. No. 4,377,783. Mar. 22, 1983.
[M] Kraxberger G. S. Method and Apparatus for measuring the moisture content of wood. U.S. Pat. No. 3,807,055. Apr. 30, 1974.
[N] Venter et. al. Dielectric Moisture Measurement, U.S. Pat. Nos. 6,703,847, 6,989,678
[R] ames W. L., Boone, R. S., Capacitive In-Kiln Wood Moisture content Monitors, Wood Science Vol. 14 No. 4, April 1982
[S] ox P. T., Dielectric cross-plot water cut monitoring apparatus and method, U.S. Pat. No. 5,272,444, Dec. 21, 1993.
[T] ox P. T., Water-Cut monitoring means and method, U.S. Pat. No. 5,070,725, Dec. 21, 1993.
[U] ames W. L. Electric Moisture Meters for Wood. United States Department of Agriculture, Forests Products Laboratory, Report FPL-GTR-6.
[V] htianien A. J., Continuous action capacitive moisture measurement apparatus. U.S. Pat. No. 4,259,632, Mar. 31, 1981. [O] Perry W. D., Method of drying wood and Moisture Indicator. U.S. Pat. No. 3,430,357, Mar. 4, 1969.
[W] teele, P. H., Moisture and density detector U.S. Pat. No. 7,068,050, Jun. 27, 2006
[Y] ogan R., In-kiln moisture measurement calibration system, Patent Application 20060201022

The invention claimed is:

1. A system for measuring the reactive impedance $Z_x$ of a dielectric material between a pair of electrodes which are inserted in the dielectric material, wherein said system comprises a known impedance $Z_s$ connected in a series circuit with said electrodes, an AC voltage source connected to apply an AC voltage across said series circuit, a phase detecting circuit connected to said series circuit operable to generate a signal representing a phase angle between AC voltages applied to different parts of said series circuit, and a processor connected to receive said signal and operable to determine a value corresponding to at least one of an independent capacitive, independent resistive and independent inductive component of said reactive impedance $Z_x$ in accordance with a predetermined arithmetic algorithm which expresses said value as a function of said phase angle, said voltages and said series impedance $Z_s$.

2. The system as recited in claim 1, wherein the voltages applied to different parts of said series circuit comprise a voltage applied across said electrodes and the voltage applied across said series circuit.

3. The system as recited in claim 1, wherein the dielectric material is wood and the value is a moisture content of wood.

4. A method of measuring the reactive impedance $Z_x$ of a material using the system according to claim 1, comprising placing a pair of electrodes in said material, connecting a known impedance $Z_s$ in series with said pair of electrodes, applying a AC voltage across said series circuit, detecting AC voltages applied to different parts of said series circuit, determining a phase angle between said AC voltages applied to different parts of said circuit, and calculating a value corresponding to at least one of an independent capacitive component, an independent inductive component and an independent resistive component of the reactive impedance $Z_x$ between said electrodes in accordance with a predetermined arithmetic algorithm which expresses said value as a function of said phase angle, said voltages and said series impedance $Z_s$.

5. The method as recited in claim 4, wherein said voltages applied to parts of said series circuit comprise the voltage applied across said series circuit and a voltage applied across said electrodes.

6. The method as recited in claim 5, wherein at least one of said voltages comprises a sinusoidal voltage.

7. The method as recited in claim 4, wherein said independent capacitive component is calculated according to the equation $$C_x = \left| \frac{\sin(\phi)\cos(\tau)V_1 + \sin(\tau)\cos(\phi)V_1 - V_2\sin(\tau)}{U\omega V_2} \right| \quad (26)$$

$C_X$ is the value of the independent capacitive component;
$V_1$ is the amplitude of the applied voltage;
$V_2$ is the amplitude of the voltage across the electrodes;
$\phi$ is the phase angle between the voltages $V_1$ and $V_2$;
U is the magnitude of the impedance $Z_S$;
$\tau$ is the angle of the Impedance $Z_S$;
$\omega$ is the radial frequency.

8. The method as recited in claim 4, wherein said independent resistive component is calculated according to the equation $$R_x = \left| \frac{UV_2}{-\cos(\phi)\cos(\tau)V_1 + V_2\cos(\tau) + \sin(\phi)\sin(\tau)V_1} \right| \quad (27)$$

$R_X$ is the value of the independent resistive component;
$V_1$ is the amplitude of the applied voltage;
$V_2$ is the amplitude of the voltage across the electrodes;
$\phi$ is the phase angle between the voltages $V_1$ and $V_2$;
U is the magnitude of the impedance $Z_S$;
$\tau$ is the angle of the Impedance $Z_S$;
$\omega$ is the radial frequency.

9. The method as recited in claim 4, wherein said independent inductive component is calculated according to the equation $$L_x = \left| \frac{UV_2}{\omega[\sin(\phi)\cos(\tau)V_1 + \sin(\tau)\cos(\phi)V_1 - V_2\sin(\tau)]} \right| \quad (28)$$

$L_X$ is the value of the independent inductive component;
$V_1$ is the amplitude of the applied voltage;
$V_2$ is the amplitude of the voltage across the electrodes;
$\phi$ is the phase angle between the voltages $V_1$ and $V_2$
U is the magnitude of the impedance $Z_S$;
$\tau$ is the angle of the Impedance $Z_S$;
$\omega$ is the radial frequency.

10. The method as recited in claim 4, wherein the loss tangent tan $\delta$ is calculated according to the equation $$\tan\delta = \frac{1}{\omega R_x C_x} \quad (29)$$

$R_X$ is the value of the independent resistive component;
$C_X$ is the value of the independent capacitive component;
$\omega$ is the radial frequency.

11. The method according to claim 10, wherein a fiber saturation point of wood is determined by measuring the loss tangent of the wood and determining the point where the loss-tangent equals zero, which corresponds to the fiber saturation point of the wood.

12. The method as recited in claim 4, wherein the dielectric material is wood and a moisture content of the wood is obtained.

13. A wood drying installation comprising a kiln that behaves like a coaxial cable element for a data transmission and power transmission, wherein metal walls and doors of the kiln grounded to the soil comprise the outer coaxial conductor (shield) relative to a substantially isolated axial central conductor.

14. The wood drying installation as recited in claim 13, wherein the central conductor is a metallic rail track electrically not at short-circuit with the shield.

15. The wood drying installation as recited in claim 13, wherein the central conductor is an axial conductor electrically not at short circuit with the shield.

16. The wood drying installation as recited in claim 13, wherein the kiln as coaxial cable element is connected to a measurement device.

17. The wood drying installation as recited in claim 13, wherein the kiln as a coaxial cable element is connected to a measurement device is a dielectric moisture meter.

18. A method for determining the fiber saturation point of wood comprising measuring the loss tangent of the wood with an impedance measurement device and determining the point where the time derivative of the loss-tangent equals zero, which corresponds to the fiber saturation point of the wood.

19. The method according to claim 18, furthermore comprising determining a density of the wood using a predetermined relationship between fiber saturation point and density of wood.

* * * * *